(12) United States Patent
Justis et al.

(10) Patent No.: US 8,617,218 B2
(45) Date of Patent: Dec. 31, 2013

(54) BONE ANCHOR EXTENDERS

(75) Inventors: Jeff R Justis, Germantown, TN (US); Douglas D Kave, Byhalia, MS (US)

(73) Assignee: Warsaw Orthoepdic, Inc., Warsaw, IN (US)

( * ) Notice: Subject to any disclaimer, the term of this patent is extended or adjusted under 35 U.S.C. 154(b) by 219 days.

(21) Appl. No.: 13/107,181

(22) Filed: May 13, 2011

(65) Prior Publication Data

US 2012/0290011 A1    Nov. 15, 2012

(51) Int. Cl.
*A61B 17/70* (2006.01)

(52) U.S. Cl.
USPC .......................... 606/278; 606/86 A

(58) Field of Classification Search
USPC .......................... 606/86 A, 95, 104, 246–279
See application file for complete search history.

(56) References Cited

U.S. PATENT DOCUMENTS

| | | | |
|---|---|---|---|
| 4,448,191 A | 5/1984 | Rodnyansky et al. | |
| 5,020,519 A | 6/1991 | Hayes et al. | |
| 5,242,443 A | 9/1993 | Kambin | |
| 5,720,751 A | 2/1998 | Jackson | |
| 5,910,141 A | 6/1999 | Morrison et al. | |
| 6,183,472 B1 | 2/2001 | Lutz | |
| 6,226,548 B1 | 5/2001 | Foley et al. | |
| 6,235,028 B1 | 5/2001 | Brumfield et al. | |
| 6,485,491 B1 | 11/2002 | Farris et al. | |
| 6,530,929 B1 | 3/2003 | Justis et al. | |
| 6,648,888 B1 | 11/2003 | Shluzas | |
| 6,660,006 B2 | 12/2003 | Markworth et al. | |
| 6,740,086 B2 | 5/2004 | Richelsoph | |
| 6,740,089 B2 | 5/2004 | Haider | |
| 6,821,277 B2 | 11/2004 | Teitelbaum | |
| 7,160,300 B2 | 1/2007 | Jackson | |
| 7,250,052 B2 | 7/2007 | Landry et al. | |
| 7,465,306 B2 * | 12/2008 | Pond et al. ................. | 606/86 A |
| 7,993,344 B2 * | 8/2011 | Pond et al. ................. | 606/86 A |
| 8,226,656 B2 * | 7/2012 | Mcbride ..................... | 606/86 A |
| 2002/0161368 A1 | 10/2002 | Foley et al. | |
| 2003/0130659 A1 | 7/2003 | Haider | |
| 2003/0199873 A1 | 10/2003 | Richelsoph | |
| 2003/0199884 A1 | 10/2003 | Davison et al. | |
| 2003/0225408 A1 | 12/2003 | Nichols et al. | |
| 2004/0039384 A1 | 2/2004 | Boehm, Jr. et al. | |
| 2004/0049191 A1 | 3/2004 | Markworth et al. | |
| 2004/0138662 A1 | 7/2004 | Landry et al. | |
| 2004/0143265 A1 | 7/2004 | Landry et al. | |
| 2004/0162560 A1 | 8/2004 | Raynor et al. | |
| 2004/0172022 A1 | 9/2004 | Landry et al. | |
| 2004/0215190 A1 | 10/2004 | Nguyen et al. | |
| 2004/0267275 A1 | 12/2004 | Cournoyer et al. | |

(Continued)

FOREIGN PATENT DOCUMENTS

DE    202005007495 U1    8/2005

*Primary Examiner* — Eduardo C Robert
*Assistant Examiner* — James Palmer

(57) ABSTRACT

In one form, systems and methods for positioning a connecting member adjacent the spinal column include at least one anchor that is engageable to bony structure and has a receiver for receiving the connecting member. A pair of elongated members is engaged to the receiver and defines a pathway that extends proximally from the receiver. The connecting member is movable along the elongated members to the receiver of the bone anchor. The elongated members are removable from the receiver of the bone anchor after the connecting member is positioned in the receiver to provide a low profile anchor and connecting member assembly when finally implanted in the patient. However, other embodiments, forms and applications are also envisioned.

20 Claims, 12 Drawing Sheets

(56) References Cited

U.S. PATENT DOCUMENTS

| | | |
|---|---|---|
| 2005/0010219 A1 | 1/2005 | Dalton |
| 2005/0010221 A1 | 1/2005 | Dalton |
| 2005/0033299 A1 | 2/2005 | Shluzas |
| 2005/0080418 A1 | 4/2005 | Simonson et al. |
| 2005/0085813 A1 | 4/2005 | Spitler et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0137594 A1 | 6/2005 | Doubler et al. |
| 2005/0154389 A1 | 7/2005 | Selover et al. |
| 2005/0171540 A1 | 8/2005 | Lim et al. |
| 2005/0182407 A1 | 8/2005 | Dalton |
| 2005/0182410 A1 | 8/2005 | Jackson |
| 2005/0192570 A1 | 9/2005 | Jackson |
| 2005/0192579 A1 | 9/2005 | Jackson |
| 2005/0192589 A1 | 9/2005 | Raymond et al. |
| 2005/0273101 A1 | 12/2005 | Schumacher |
| 2006/0025771 A1 | 2/2006 | Jackson |
| 2006/0036252 A1 | 2/2006 | Baynham et al. |
| 2006/0058794 A1 | 3/2006 | Jackson |
| 2006/0084980 A1 | 4/2006 | Melkent et al. |
| 2006/0293664 A1 | 12/2006 | Schumacher |
| 2007/0049931 A1* | 3/2007 | Justis et al. ............ 606/61 |
| 2007/0106123 A1 | 5/2007 | Gorek et al. |
| 2007/0191840 A1 | 8/2007 | Pond, Jr. et al. |
| 2008/0119849 A1 | 5/2008 | Beardsley et al. |
| 2008/0262318 A1 | 10/2008 | Gorek et al. |
| 2009/0221877 A1 | 9/2009 | Woods |
| 2009/0221878 A1 | 9/2009 | Gorek |
| 2009/0222046 A1 | 9/2009 | Gorek |
| 2010/0114183 A1* | 5/2010 | Wassinger et al. ......... 606/86 A |

* cited by examiner

BONE ANCHOR EXTENDERS

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. However, there remains a need for further improvements in instruments, systems and methods for stabilizing bony structures using minimally invasive techniques.

SUMMARY

In one embodiment, there are provided systems and methods for positioning a connecting member adjacent the spinal column that include at least one anchor that is engageable to bony structure and has a receiver for receiving the connecting member. A pair of elongated members is engaged to the receiver and defines a pathway that extends proximally from the receiver. The connecting member is movable along the elongated members to the receiver of the bone anchor. The elongated members are removable from the receiver of the bone anchor after the connecting member is positioned in the receiver to provide a low profile anchor and connecting member assembly when finally implanted in the patient.

Another embodiment is directed to a unique anchor extender for use in surgical procedures in a patient. Other embodiments include unique methods, techniques, systems, devices, kits, assemblies, equipment, and/or apparatus involving anchor extenders.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
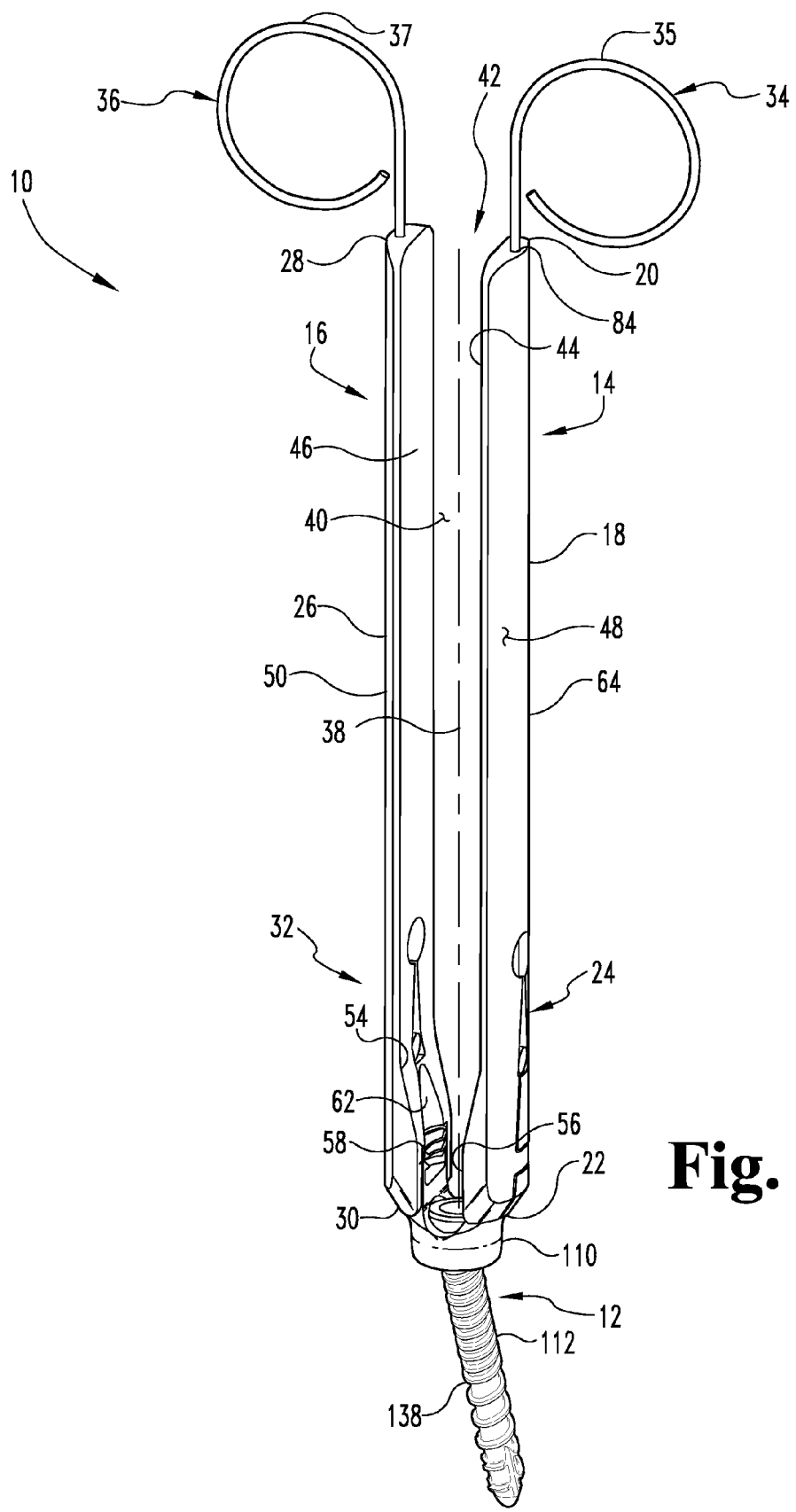
FIG. 1 is a perspective view of one embodiment spinal surgical system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

In one form, spinal surgical systems are provided that include at least one anchor engageable to a bony structure, such as one or more vertebrae of a spinal column, and at least one anchor extender to facilitate positioning of the at least one anchor and/or to guide placement of one or more connecting members from a location outside patient, or within the patient but remote from an implantation location, to or more adjacent to an implantation location in the patient. The connecting member can be an elongated spinal rod, tether, bar, plate, wire, or other suitable device that is to be engaged to one or more bone anchors. The systems are particularly suited for minimally invasive surgical procedures, but are not restricted to such procedures. Furthermore, although its use and application is described with regard to spinal surgery, applications in surgeries other than spinal surgery are also contemplated.

In another form, surgical systems are provided that include at least one bone anchor engageable to a spinal column. The bone anchor includes a bone engaging portion and a receiver for receiving the connecting member. A pair of anchor extenders is engaged to and extends proximally from the receiver to a proximal end located so that it is readily accessible by the surgeon. The anchor extenders define a space that extends proximally from a proximal end opening of the receiver located between the anchor extenders. The anchor extenders can provide a path for insertion of the connecting member that is referenced to the location of the receiver, or a platform for engagement of an inserter to proximal ends of the anchor extenders so that the inserter is referenced to the receiver locations within the patient. The connecting member is positionable into the space defined by the anchor extenders and movable along the anchor extenders through a proximal end opening of the receiver and into the receiver. The connecting member can also be positioned directly into the receiver from a side of the receiver. The connecting member can then be secured to the bone anchor with an engaging member engaged to the receiver. The anchor extenders are removable from the receiver so that the anchor assembly has a low-profile in the patient post-surgery.

In another aspect, surgical systems are provided that include at least a pair of bone anchors engaged to the spinal column. The bone anchors each include a pair of anchor extenders engaged to a receiver of the bone anchor so that the anchor extenders extend proximally from the receiver. The anchor extenders provide a platform for engagement of an inserter, or can serve as a guide for the placement of a connecting member from a position remote from the implantation location to a position more adjacent the spinal column, such as the implantation location. The anchor extenders are configured so that when the connecting member is guided adjacent to the spinal column, the connecting member extends through the bone anchors. The connecting member is secured to the bone anchors and provides stabilization of the spinal column segment to which the bone anchors are attached. The anchor extenders are removed from the bone anchor assemblies after implantation of the connecting member so that the connecting member implantation and extension removal is accomplished without invasively accessing the patient's body.

In yet another aspect, an anchor extender includes an elongated body extending between a proximal end and a distal end. The elongated body also includes a bifurcated distal end portion extending from a proximal portion, and the bifurcated distal end portion includes a pair of engaging members that define an anchor engaging portion. The engaging members are flexibly movable relative to the proximal portion between a first configuration for receiving a portion of a bone anchor and a second configuration for engaging with the portion of the bone anchor. The anchor extender also includes an elongated pin that extends through the proximal portion and is axially displaceable relative to the elongated body between a first position and a second position. In its second position, the elongated pin engages with each of the engaging members and retains or fixes the relative positioning of the engaging members. In one form, axial displacement of the elongated pin from its second position to its first position applies a separation force between the engaging members. Amongst other things, the anchor extender may be engaged to the bone anchor to facilitate positioning of the bone anchor and/or guide a connecting element to the bone anchor. In one form, a single anchor extender is engageable with the bone anchor, although forms in which a pair of anchor extenders is engageable with the bone anchor are also possible.

Referring to FIG. 1, one embodiment of a spinal surgical system 10 is shown. System 10 includes a bone anchor 12 and a pair of anchor extenders 14, 16 extending proximally from bone anchor 12. In the illustrated form, anchor extenders 14, 16 are separate from one another and may be individually engaged with bone anchor 12. In other non-illustrated forms however, it should be understood that anchor extenders 14, 16 may be coupled or otherwise formed together such that anchor extenders 14, 16 collectively define a single anchor extender and anchor extenders 14, 16 are simultaneously positioned relative to bone anchor 12. It should also be understood that forms of system 10 in which only one of anchor extenders 14, 16 is engaged with bone anchor 12 are also possible. One or both of anchor extenders 14, 16 can be engaged with bone anchor 12 following its engagement with underlying bone or bony tissue, although forms in which one or both of anchor extenders 14, 16 are engaged with bone anchor 12 before its implantation and then used to manipulate or otherwise handle bone anchor 12 during implantation are also contemplated.

Anchor extender 14 includes an elongated body 18 that extends between a proximal end 20 and an opposite distal end 22 and includes a distal anchor engaging portion 24. Anchor extender 14 also includes an elongated locking member or pin 34 positioned in elongated body 18. Elongated locking member 34 includes a proximal end 35 positioned proximal of proximal end 20 and a distal end portion 92 (FIG. 2) engageable with anchor engaging portion 24. Further details regarding anchor engaging portion 24 and engagement of elongated pin 34 therewith will be provided below. Anchor extender 16 includes an elongated body 26 that extends between a proximal end 28 and an opposite distal end 30 and includes a distal anchor engaging portion 32. Anchor extender 16 also includes an elongated locking member or pin 36 positioned in elongated body 26. Elongated locking member 36 includes a proximal end 37 positioned proximal of proximal end 28 and a distal end portion (not shown) engageable with anchor engaging portion 32. In one form, elongated bodies 18, 26 include a length sufficient to locate proximal ends 20, 28 outside the skin and tissue of the patient when anchor engaging portions 24, 32 are engaged with bone anchor 12 and bone anchor 12 is secured to bony structure within the patient. In one embodiment, this length is at least 30 millimeters. In another embodiment, the length of anchor extenders 14, 16 is at least 50 millimeters. Other lengths are also contemplated. In one specific embodiment, the length is at least 100 millimeters, and extends about 120 millimeters from bone anchor 12 to the proximal ends 20, 28 of the anchor extenders 14, 16.

Figure 11:
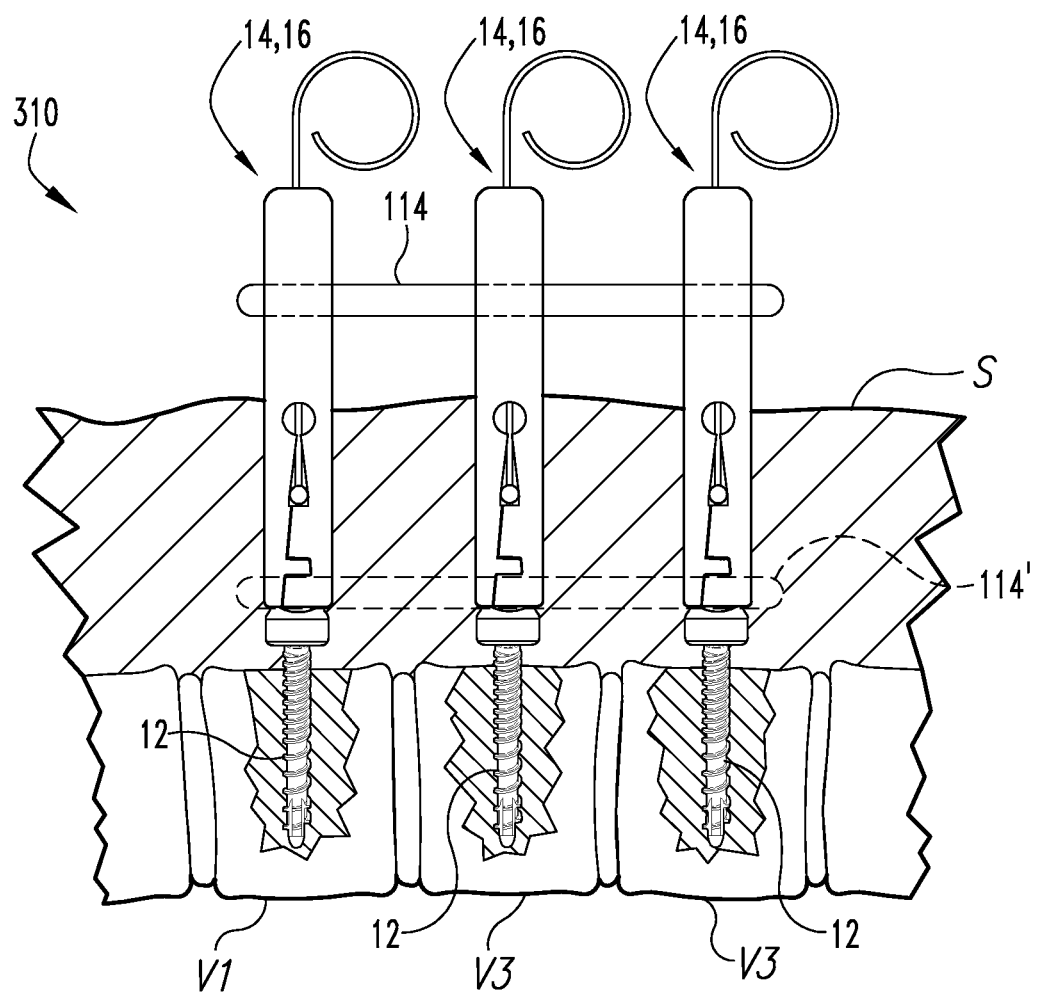
FIG. 11 is a diagrammatic elevation view of an alternative embodiment spinal surgical system employing multiple bone anchor engaged to a spinal column to guide a connecting member in a minimally invasive procedure.
Figure 12:
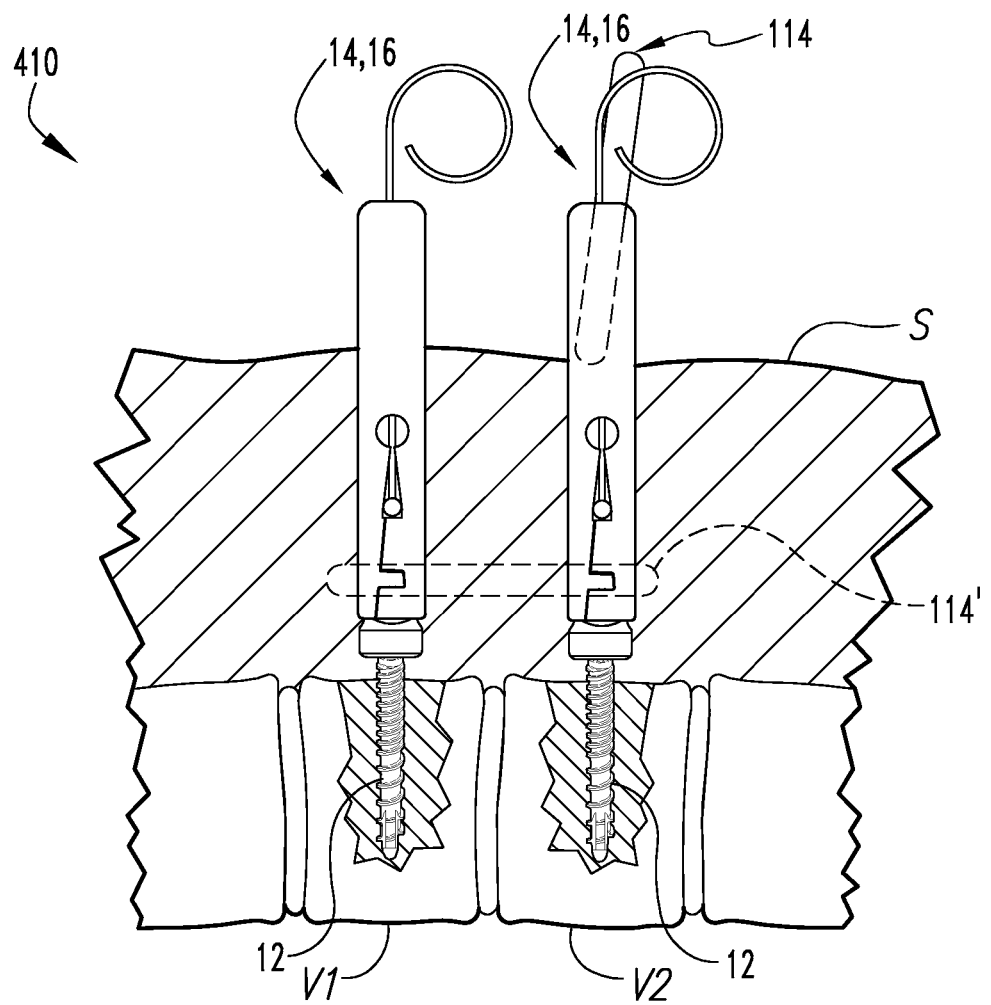
FIG. 12 is a diagrammatic elevation view of another embodiment spinal surgical system employing multiple bone anchors engaged to a spinal column to guide a connecting member in a minimally invasive procedure.

As illustrated in FIG. 1 for example, anchor extenders 14, 16 extend longitudinally on opposite sides of a central longitudinal axis 38 and form a space 40 therebetween to receive a connecting member 114 (FIGS. 11-12). In the illustrated embodiment, anchor extenders 14, 16 form a proximal opening 42 therebetween to allow connecting member 114 to be placed through the proximal end opening 42 into space 40 between anchor extenders 14, 16. As indicated above, in alternative, non-illustrated forms, anchor extenders 14, 16 can be coupled or otherwise formed together. In one such form, a proximal portion (not shown) is provided that extends between and connects anchor extenders 14, 16 to close the proximal end opening 42, requiring connecting member 114 to be positioned into space 40 from the sides of anchor extenders 14, 16 with connecting member 114 oriented in a length-wise manner that is transverse to longitudinal axis 38.

Anchor extenders 14, 16 include planar facing surfaces 44, 46, respectively, that extend parallel to one another and parallel to longitudinal axis 38 and define space 40 therebetween. Anchor extenders 14, 16 also include features to facilitate guiding and placement of connecting member 114 into bone anchor 12. Anchor extenders 14, 16 include a receiving portion along parallel surfaces 44, 46 that forms a location to receive and provide initial guidance of the placement of connecting member 114 into and along space 40. Anchor extenders 14, 16 also include a tapered portion to direct connecting member 114 from its initial placement through space 40 into alignment with a passage of bone anchor 12. Anchor extender 14 includes a tapered surface portion 52 extending distally from inner surface 44 and anchor extender 16 includes a tapered surface portion 54 extending distally from inner surface 46. Tapered surface portions 52, 54 converge toward one another and join with the respective alignment surface portions 56, 58, respectively, at or near the proximal end of bone anchor 12. Alignment surface portions 56, 58 extend parallel to one another to form an extension of inner surfaces of bone anchor 12 defining the passage into which connecting member 114 is positioned. Anchor extenders 14, 16 also include concave recesses 60, 62 in respective ones of the tapered surface portions 52, 54. Recesses 60, 62 are concavely curved in a direction between the elongated sides of the respective anchor extender 14, 16 so that the respective recess 60, 62 aligns with respective ones of side portions of bone anchor 12. In addition, anchor extenders 14, 16 include outer, oppositely facing surfaces 48, 50, respectively, that define a convex curvature extending around longitudinal axis 38 and a generally linear profile paralleling longitudinal axis 38. The curved outer surfaces 48, 50 provide a smooth surface contour that holds back tissue from encroaching into space 40 while minimizing trauma to the tissue pressing against anchor extenders 14, 16.

Figure 4:
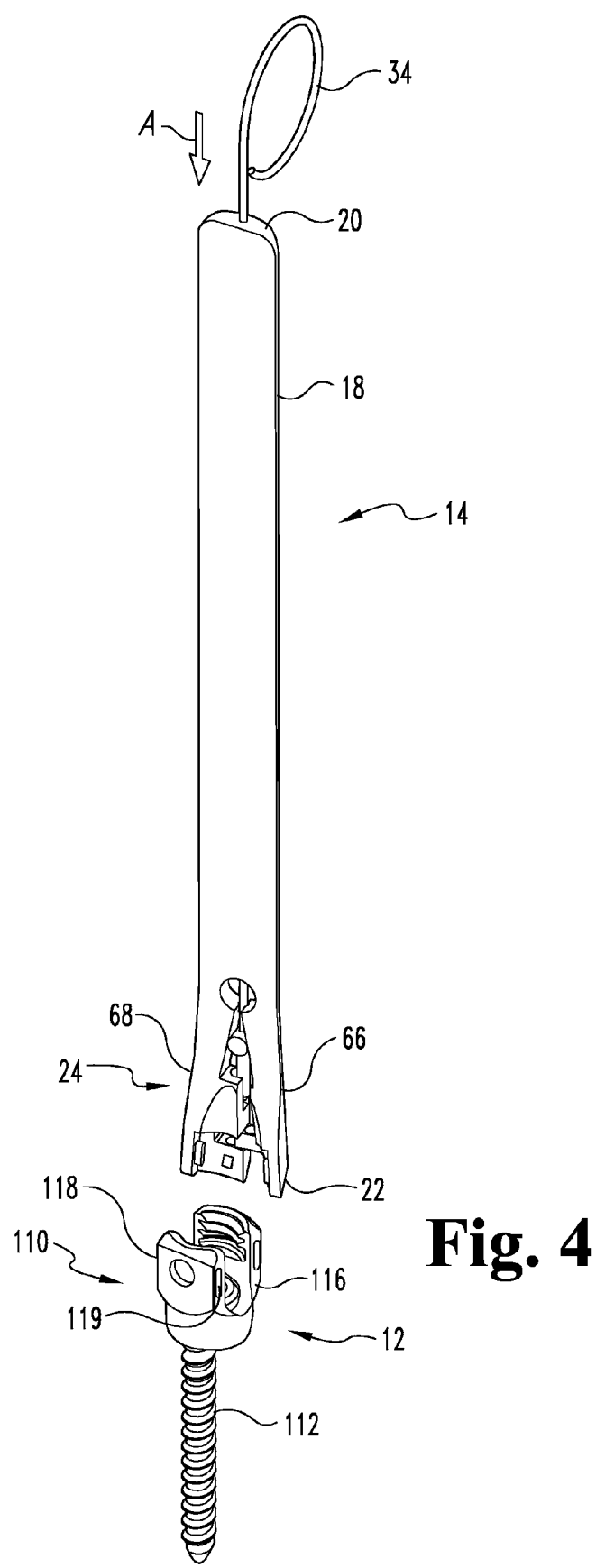
FIG. 4 is a perspective view of the anchor extender illustrated in FIG. 2 positioned adjacent to a bone anchor with the anchor engaging portion configured for receiving the bone anchor.
Figure 5:
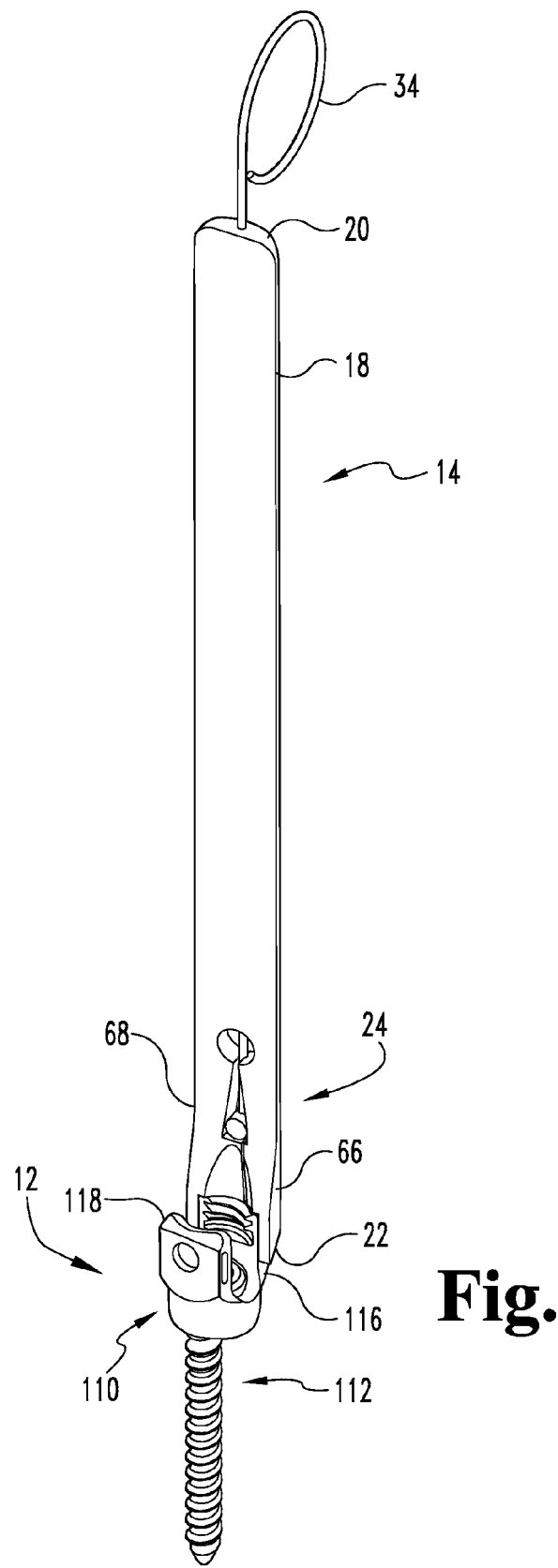
FIG. 5 is a perspective view of the anchor extender illustrated in FIG. 2 with the anchor engaging portion engaged with the bone anchor.
Figure 6:
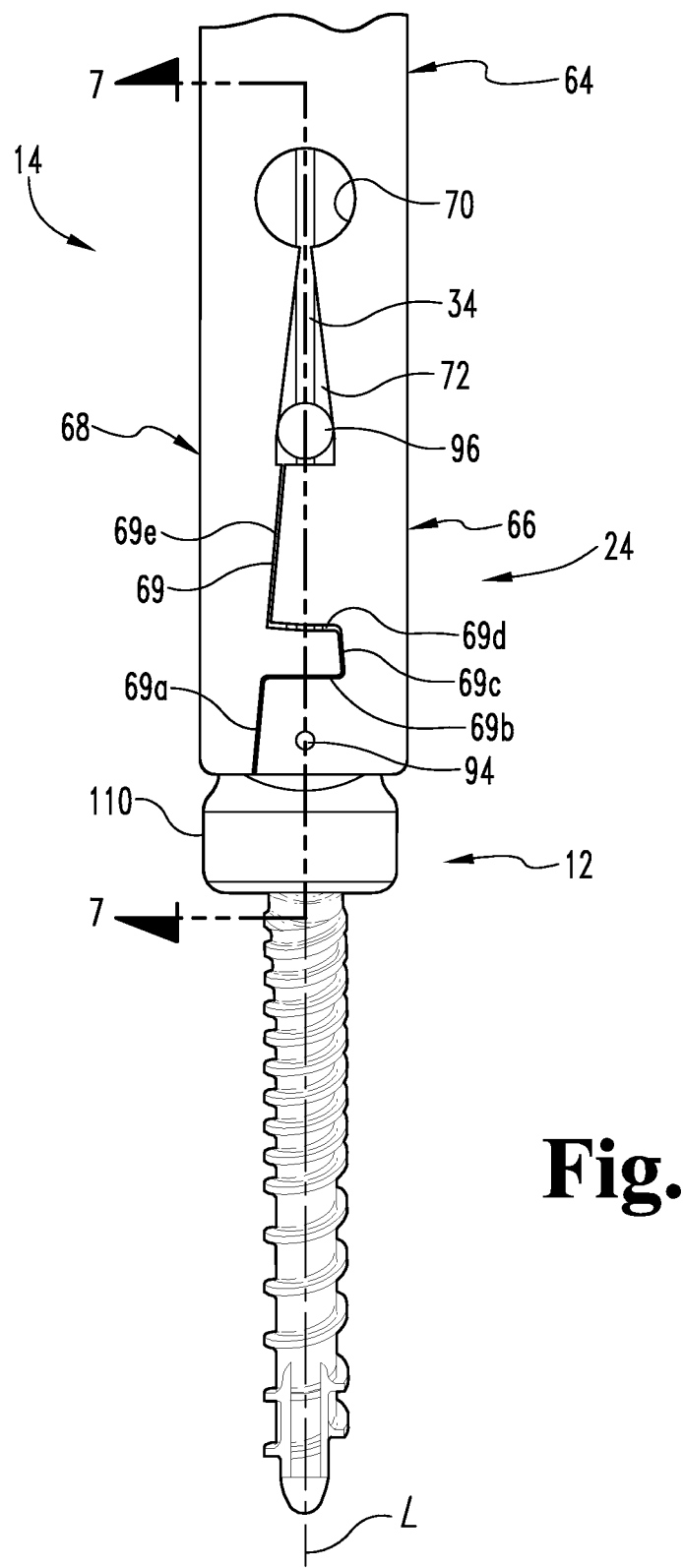
FIG. 6 is an enlarged, side plan view of the anchor extender engaged with the bone anchor.

With further reference to FIGS. 2-7, further details regarding anchor extender 14 will be provided. While not discussed in detail below, it should be appreciated that anchor extender 16 is generally configured the same as anchor extender 14. Similarly, the following description of anchor extender 14 will also generally be applicable to anchor extender 16. Anchor engaging portion 24 of anchor extender 14 is bifurcated by an elongate slit 69 into a pair of engaging members 66, 68 that extend distally from a proximal portion 64 of elongated body 18. Elongated body 18 also includes an aperture 70 that extends transversely therethrough and may facilitate flexible movement of engaging members 66, 68 relative to one another and to proximal portion 64 of elongated body 18. Additionally or alternatively, elongated body 18 may be formed of a material having properties that facilitate flexible movement of engaging members 66, 68 relative to one another and to proximal portion 64 of elongated body 18. More particularly, in the illustrated form engaging members 66, 68 may be pivoted about their proximal ends relative to proximal portion 64 such that the distal ends of engaging members 66, 68 may be moved toward and away from one another. In this arrangement, anchor engaging portion 24 may be positioned between a first configuration for receiving a portion of bone anchor 12 where the distal ends of engaging members 66, 68 are displaced away from one another and longitudinal axis L and a second configuration for engaging with a portion of bone anchor 12 where the distal ends of engaging members 66, 68 are positioned adjacent one another as illustrated in FIG. 6. Further details regarding engagement of anchor extender 14 with bone anchor 12 will be provided below.

Anchor engaging portion 24 also includes a generally triangular shaped opening 72 that communicates with and extends distally from aperture 70. Opening 72 is formed by a surface 74 of engaging member 66 that extends obliquely to longitudinal axis L and a surface 76 of engaging member 68 that extends obliquely to longitudinal axis L and surface 74. Opening 72 is also formed by a surface 78 extending transversely to longitudinal axis L and between engaging member 66, 68. As best seen in FIG. 6 for example, elongated slit 69 includes a number of portions 69a-e positioned between distal end 22 and surface 78 of opening 72. More specifically, when anchor engaging portion 24 is in its second configuration, first portion 69a is positioned on a first side of longitudinal axis L and extends obliquely toward longitudinal axis L in a proximal direction from distal end 22 to a second portion 69b. Second portion 69b extends between first and second sides of longitudinal axis L and transversely to longitudinal axis L to a third portion 69c. Third portion 69c is positioned on the second side of the longitudinal axis L and extends obliquely to first portion 69a and obliquely toward longitudinal axis L in a proximal direction to a fourth portion 69d. Fourth portion 69d extends between first and second sides of longitudinal axis L and transversely to longitudinal axis L to a fifth portion 69e. Fifth portion 69e is positioned on the first side of longitudinal axis L and extends obliquely toward longitudinal axis L in a proximal direction from fourth portion 69d to opening 72. In this arrangement, elongated slit 69 defines a tab 80 extending transversely from engaging member 68 and a receptacle 82 in engaging member 66 configured to receive tab 80 when anchor engaging portion 24 is in its second configuration as illustrated in FIG. 6 for example. Moreover, except for a portion of tab 80, engaging member 68 is positioned on the first side of longitudinal axis L when anchor engaging portion 24 is in its second configuration.

Elongated body 18 also includes an elongated passage 84 that extends from proximal end 20 through proximal portion 64 into communication with opening 70. In addition, engaging member 66 includes a first passage 86 that extends distally from opening 72. First passage 86 is positioned proximal of and in axial alignment with a second passage 88. In the illustrated form, second passage 88 opens at distal end 22 of elongated body 18, although it should be understood that forms in which second passage 88 is provided as a blind hole are also possible. Engaging member 68 includes a passage 90 that extends through tab 80. Elongated pin 34 extends through proximal portion 64 in elongated passage 84 and includes an enlarged distal end portion 92 having a tapered distal tip 94. Elongated pin 34 also includes a wedge member 96 which is enlarged relative to distal end portion 92 and positioned proximal of distal end portion 92. In the illustrated form, wedge member 96 includes a circular configuration, although it should be understood that alternative configurations for wedge member 96 are possible, including rectangular and triangular configurations, just to provide a few possibilities. Wedge member 96 is slidably positioned on elongated pin 34 such that distal end portion 92 may be moved relative to wedge member 96. More specifically, upon distal displacement of elongated pin 34, wedge member 96 may initially move distally until it engages with surface 78 which prevents further distal movement of wedge member 96 as distal movement of elongated pin 34 is continued. As elongated pin 34 is proximally moved, a proximal end portion of distal end portion 92 engages with wedge member 96 such that wedge member 96 is moved proximally with elongated pin 34.

Figure 7:
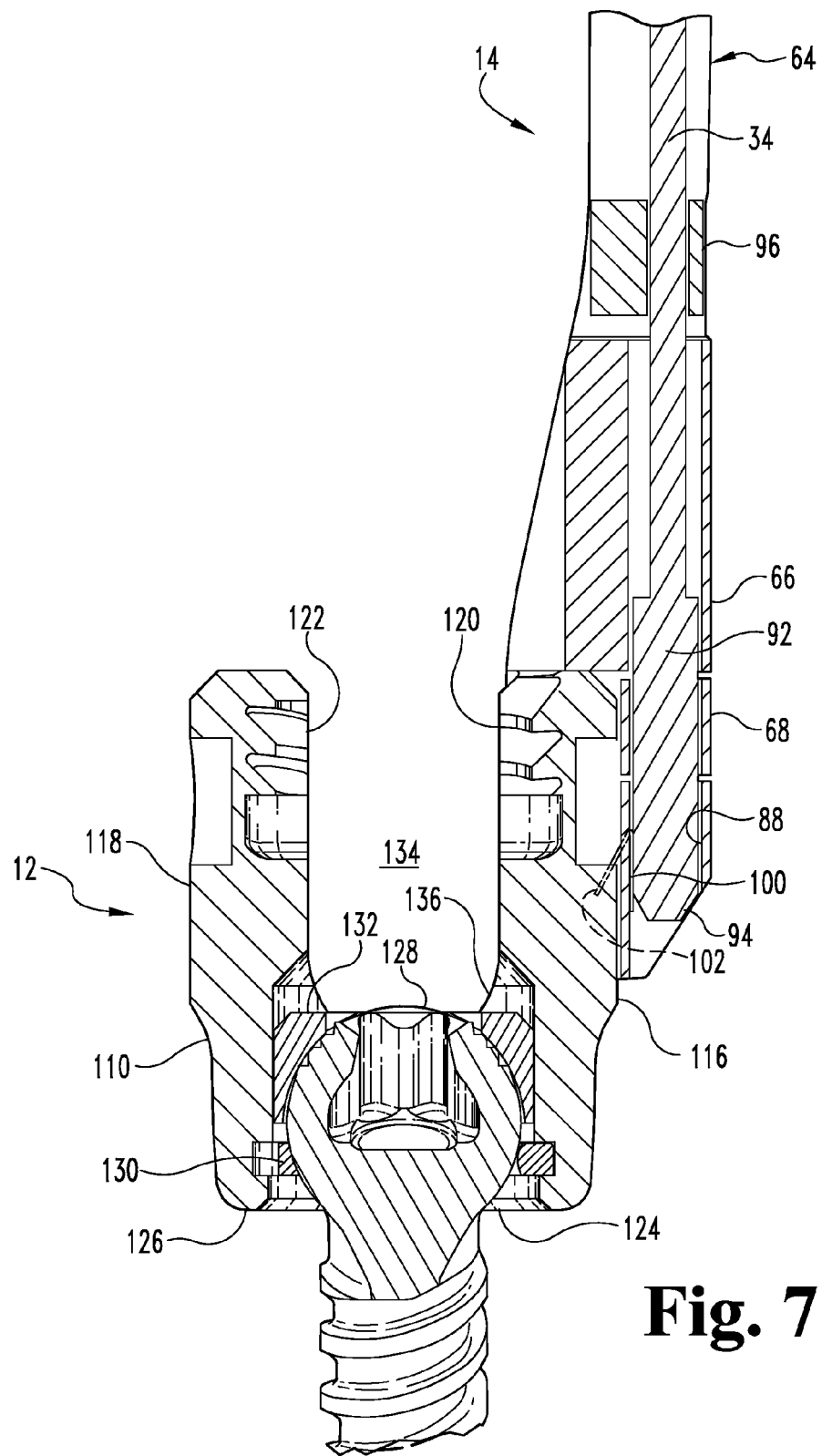
FIG. 7 is a section view taken along view line 7-7 in FIG. 6.

Anchor engaging portion 24 also includes a receptacle 92 formed between engaging members 66, 68 and configured to receive a portion of bone anchor 12. Engaging member 66 includes a first elongate tab 94 positioned in receptacle 92 and engaging member 68 includes a second elongate tab 96 positioned in receptacle 92 and opposite of first elongate tab 94. Tabs 94, 96 are configured to be received in corresponding receptacles on bone anchor 12 when anchor extender 14 is engaged with bone anchor 12. In the illustrated form, engaging member 66 also includes a contact member 98 positioned in receptacle 92. As illustrated in FIG. 7, contact member 98 includes a first portion 100 positioned in second passage 88 of engaging member 66 and a second portion 102 extending obliquely to first portion 100 and from second passage 88 through a sidewall surrounding second passage 88. In one form, contact member 98 may be configured such that first and second portions 100, 102 are flexibly movable relative to one another. It should also be understood that forms in which contact member 96 is omitted from anchor extender 14 are also possible.

Figure 2:
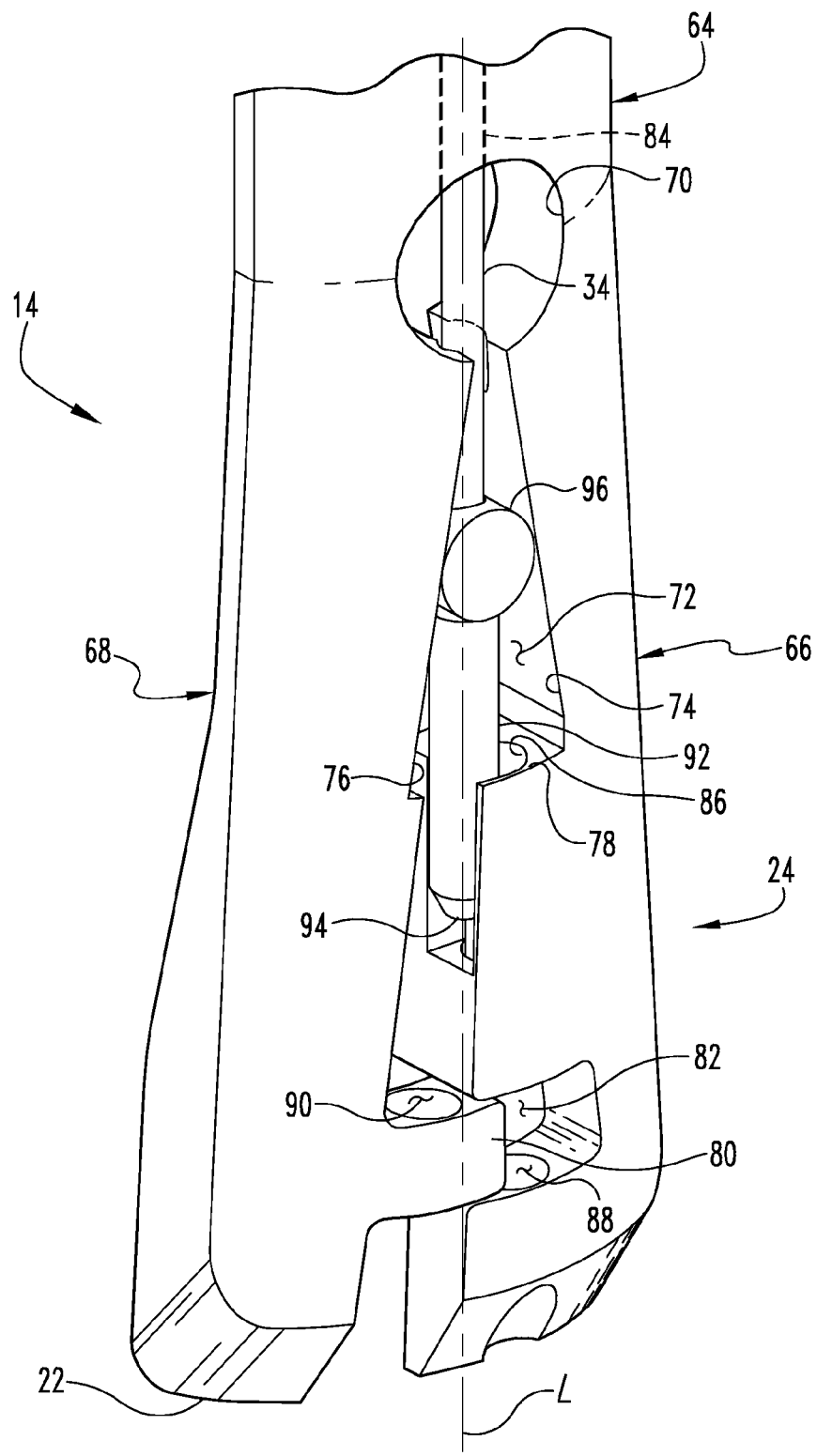
FIG. 2 is an enlarged, perspective view of a first side of an anchor engaging portion of an anchor extender illustrated in FIG. 1.
Figure 3:
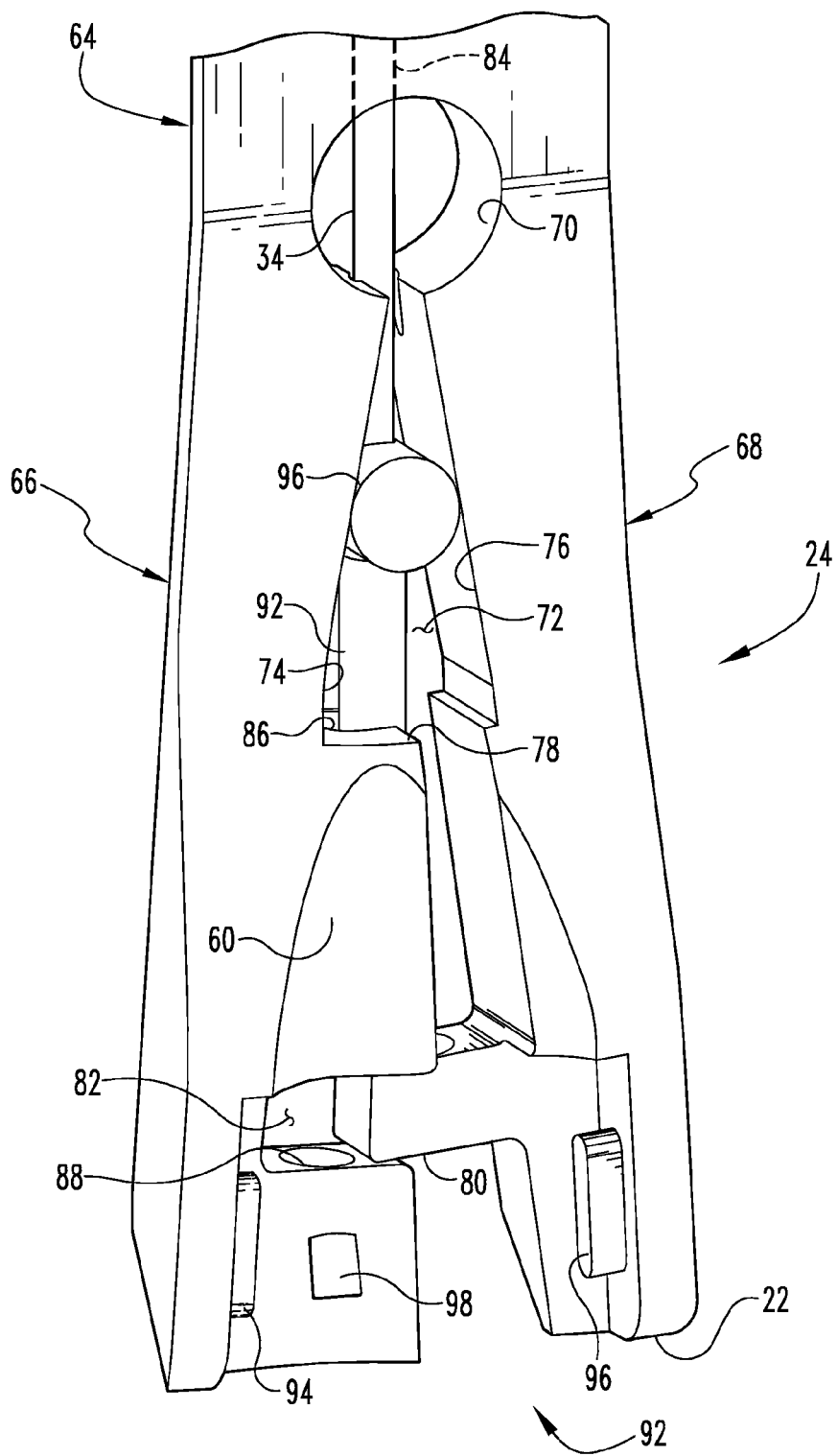
FIG. 3 is an enlarged, perspective view of a second side of the anchor engaging portion of the anchor extender illustrated in FIG. 2.

While not previously discussed, it should be appreciated that elongated pin 34 is axially displaceable relative to elongated body 18 and engageable with anchor engaging portion 24 to move anchor engaging portion 24 between its first configuration for receiving a portion of bone anchor 12 and its second configuration for engaging with the portion of bone anchor 12. More particularly, as illustrated in FIGS. 2-3 for example, anchor engaging portion 24 can be positioned in its first configuration for receiving a portion of bone anchor 12 by proximally displacing elongated pin 34 relative to engaging members 66, 68 such that wedge member 96 is brought into engagement with surfaces 74, 76 of engaging members 66, 68, respectively. As wedge member 96 engages with surfaces 74, 76 and elongated pin 34 is further proximally displaced, wedge member 96 forces engaging members 66, 68 away from one another such that a space is formed and enlarged between their distal ends and the portion of bone anchor 12 can be received therebetween.

Once the portion of bone anchor 12 is positioned between engaging members 66, 68, elongated pin 34 may be distally displaced relative to elongated body 18. As elongated pin 34 is distally displaced relative to elongated body 18, the separation force applied to engaging members 66, 68 by wedge member 96 is reduced such that engaging members 66, 68 may move toward one another to position anchor engaging portion 24 toward its second configuration. In addition, tapered distal end 94 of distal end portion 92 of elongated pin 34 is positioned through passage 86 of engaging member 66, and its tapered configuration facilitates engagement with passage 90 of engaging member 68 and axial alignment of passage 90 with passage 86. Anchor engaging portion 24 may also be configured such that engaging members 66, 68 resiliently return or spring back toward one another when not being displaced by wedge member 96. Tapered distal end 94 also passes into passage 88 of engaging member 66 such that a portion of distal end portion 92 is positioned in each of passages 86, 88 and 90. In this arrangement, anchor engaging portion 24 is positioned in its second configuration and anchor extender 14 is releasably engaged to bone anchor 12 as illustrated in FIGS. 5-6 for example. It should be appreciated that anchor engaging portion 24 will be retained in its second configuration and engagement with bone anchor 12 until elongated pin 34 is proximally displaced out of engagement with engaging members 66, 68.

Figure 9:
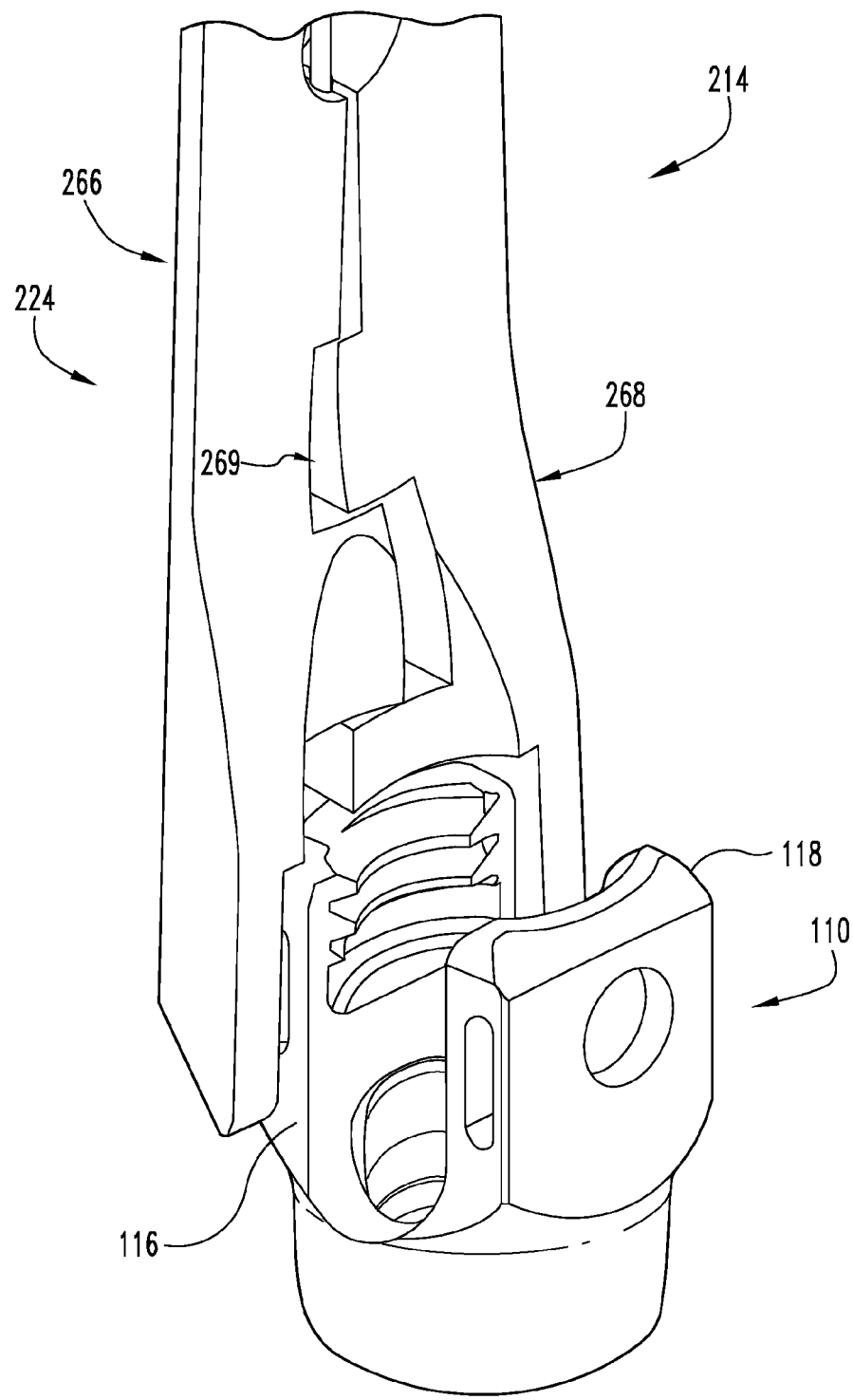
FIG. 9 is a perspective view of the anchor extender illustrated in FIG. 8 with an anchor engaging portion configured to receive a bone anchor.
Figure 10:
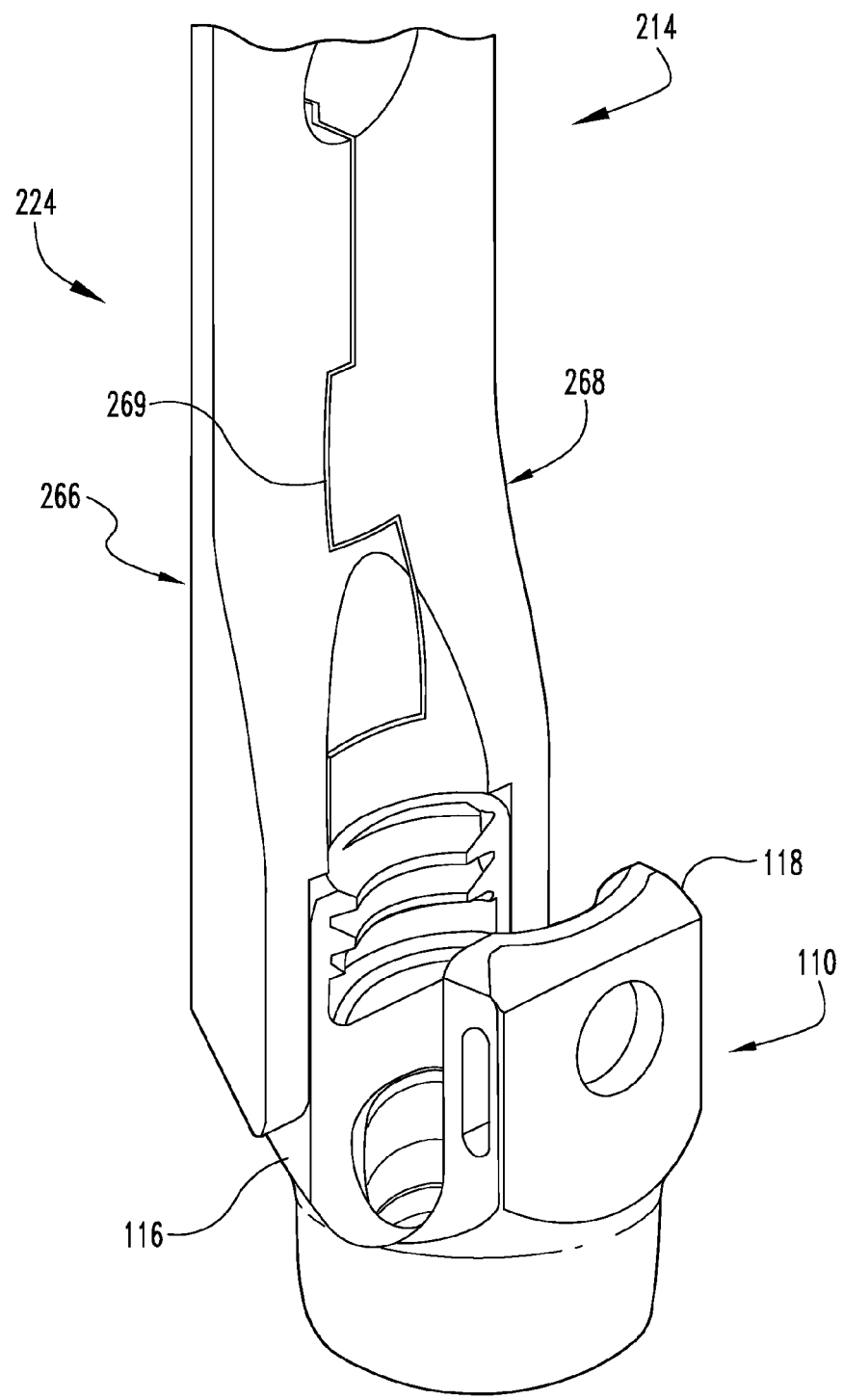
FIG. 10 is a perspective view of the anchor extender illustrated in FIG. 8 with the anchor engaging portion engaged with the bone anchor.

In view of the foregoing, it should be appreciated that anchor engaging portion 24 is moved from its first configuration to its second configuration by axially displacing elongated pin 34 relative to elongated body 18 in a distal direction, and from its second configuration to its first configuration by axially displacing elongated pin 34 relative to elongated body 18 in a proximal direction as wedge member 96 engages with engaging members 66, 68. It should be understood however that forms in which elongated pin 34 does not force engaging members 66, 68 apart as it is moved proximally relative to elongated body 18 are also contemplated. More particularly, referring collectively to FIGS. 8-10, where like numerals refer to like features previously described, an alternative embodiment anchor extender 214 is illustrated. Anchor extender 214 is substantially similar to anchor extender 14, provided however that opening 72 and wedge member 96 are not included in anchor extender 214. In addition, elongated slit 269 which bifurcates anchor engaging portion 224 into engaging members 266, 268 is alternatively arranged relative to elongated slit 69 of anchor extender 14.

Figure 8:
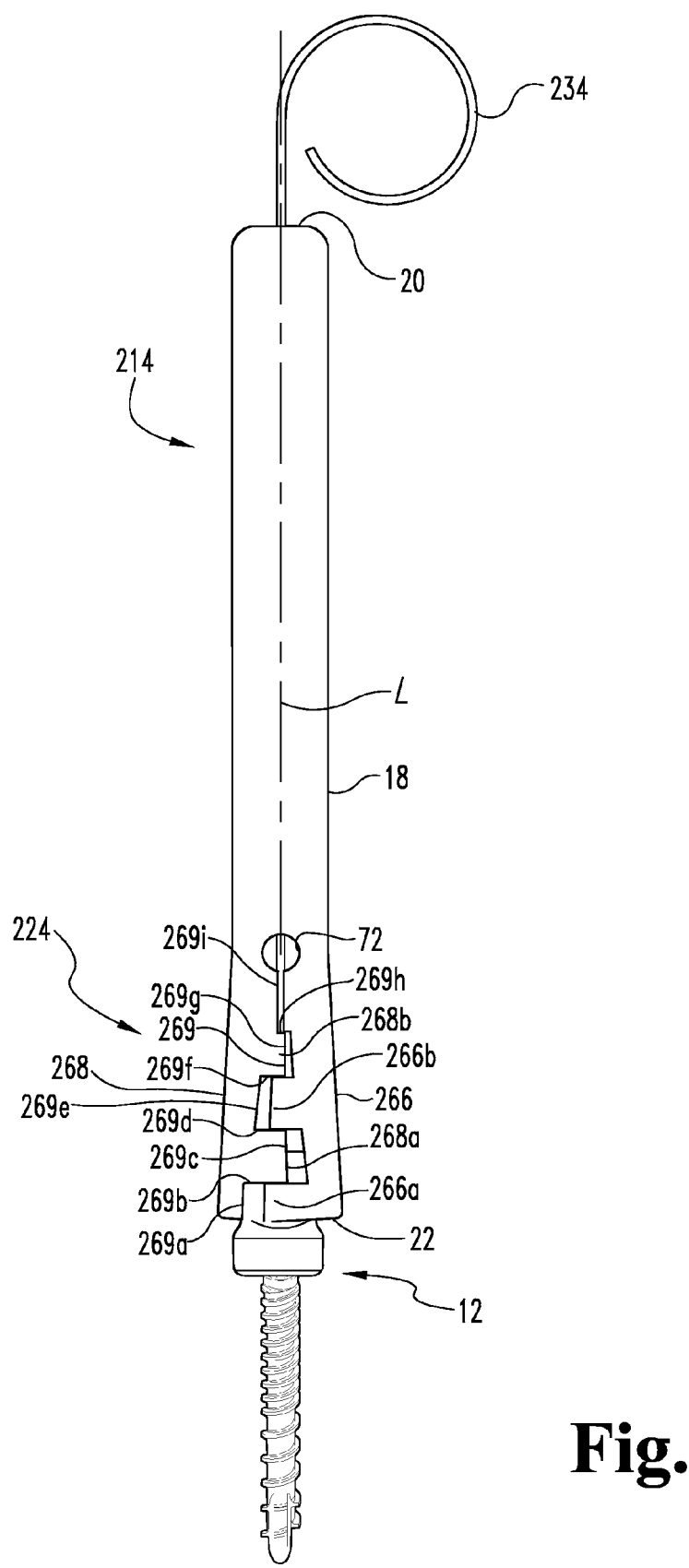
FIG. 8 is a side plan view of an alternative embodiment anchor extender.

More particularly, as best seen in FIG. 8 for example, elongated slit 269 includes a number of portions 269a-i positioned between distal end 22 and opening 72. The following description of elongate slit 269 pertains to its configuration when anchor engaging portion 224 is in its second configuration for engagement with bone anchor 12. In this configuration, elongate slit 269 includes a first portion 269a positioned on a first side of longitudinal axis L and extending obliquely toward longitudinal axis L in a proximal direction from distal end 22 to a second portion 269b. Second portion 269b extends between first and second sides of longitudinal axis L and transversely to longitudinal axis L to a third portion 269c. Third portion 269c is positioned on the second side of the longitudinal axis L and extends obliquely to first portion 269a and obliquely toward longitudinal axis L in a proximal direction to a fourth portion 269d. Fourth portion 269d extends between first and second sides of longitudinal axis L and transversely to longitudinal axis L to a fifth portion 269e. Fifth portion 269e is positioned on the first side of longitudinal axis L and extends obliquely toward longitudinal axis L in a proximal direction to a sixth portion 269f. Sixth portion 269f extends between first and second sides of longitudinal axis L and transversely to longitudinal axis L to a seventh portion 269g. Seventh portion 269g is positioned on the second side of the longitudinal axis L and extends obliquely to fifth portion 269e and obliquely toward longitudinal axis L in a proximal direction to an eighth portion 269h. Eighth portion 269h extends between first and second sides of longitudinal axis L and transversely to longitudinal axis L to a ninth portion 269i. Ninth portion 269i is positioned along the longitudinal axis L and extends in a proximal direction to aperture 70.

In view of the foregoing, it should be appreciated that elongated slot 269 generally includes a labyrinthine configuration between distal end 22 and aperture 70. Further, given this configuration, anchor engaging portion 224 is provided with an interdigitating arrangement between portions 266a-b and 268a-b of engaging members 266, 268, respectively. Anchor extender 214 generally includes a configuration that biases engaging members 266, 268 away from one another at their distal ends when not engaged by elongated pin 234. However, distal displacement of elongated pin 234 relative to elongated body 18 results in movement of engaging members 266, 268 toward one another to move anchor engaging portion 224 to its second configuration for engaging bone anchor 12. More particularly, a tapered distal end (not shown) of elongated pin 234 is successively advanced through passages (not shown) in portions 268b, 266b, 268a and 266a of engaging members 266, 268 to successively bring engaging members 266, 268 together until they engage with bone anchor 12. Engaging members 266, 268 are retained in engagement with bone anchor 12 by elongated pin 234 unless and until elongated pin 234 is proximally displaced relative to elongated body 18. As elongated pin 234 is moved out of engagement from engaging members 266, 268, engaging members 266, 268 are resiliently biased away from one another at their distal ends such that anchor engaging portion 224 returns to its first configuration. Additionally or alternatively, it should be understood that anchor extender 214 may also be rocked, twisted or otherwise manipulated to facilitate its release from bone anchor 12 as elongated pin 234 is disengaged from engaging members 266, 268.

In one embodiment, elongated bodies 18, 26 of anchor extenders 14, 16, 214 are made from a radiolucent material so that radiographic or fluoroscopic visualization of connecting member 114 is not obscured between anchor extenders 14, 16, 214, allowing the surgeon to monitor advancement of connecting member 114 along anchor extenders 14, 16, 214 and through the tissue of the patient during the procedure. Examples of suitable radiolucent materials include polyetheretherketone (PEEK), plastics, polymers, or aluminum, for example. Other materials are also contemplated, including radio-opaque materials and resorbable materials.

In one form, elongated bodies 18, 26 are made from an electrically non-conductive material. Still, in other forms, elongated bodies 18, 26 can be made, in whole or in part, of an electrically conductive material that is covered, in whole or in part, with an electrically insulative material such that at least a portion of the external surfaces of elongated bodies 18, 26 is electrically non-conductive. In one aspect of this form, the electrically insulative material can extend from proximal ends 20, 28 to distal ends 22, 30 such that the entire external surfaces of elongated bodies 18, 26 are electrically non-conductive, although forms in which the electrically insulative material only extends along a portion the external surfaces of elongated bodies 18, 26 are also possible. In either of these forms, elongated pins 34, 36, 234 may be made from an electrically conductive material. Similarly, with particular reference to anchor extender 14, in one non-limiting form of this arrangement, elongated pin 34 provides an electrical pathway between proximal end 20 of anchor extender 14 and bone anchor 12 when elongated pin 34 is engaged with contact member 96, which is also formed of an electrically conductive material. Due to the electrically non-conductive nature of elongated body 18 or the electrically non-conductive nature of at least a portion of the external surface of elongated body 18, the electrical pathway provided by elongated pin 34 will generally be shielded from shunting to the skin and tissue around anchor extender 14. Additionally or alternatively, elongated pin 34 can be provided with an electrically insulative material along its outer surface except for a portion at its proximal end for engagement with a neurostimulation or neural monitoring apparatus and a portion at its distal end that engages with contact member 96 such that the electrical pathway is further shielded or shielded from shunting to the skin and tissue around anchor extender 14.

While not discussed with regard to elongated pins 36, 234 and anchor extenders 16, 214, it should be appreciated that they may provide an electrical pathway to bone anchor 12 in a manner similar to that described in connection with elongated pin 34 and anchor extender 14. Moreover, when more than one of anchor extenders 14, 16, 214 is used with bone anchor 12, it should be understood that only one of anchor extenders 14, 16, 214 may be provided with a configuration that provides an electrical pathway to bone anchor 12. However, forms in which each anchor extender 14, 16, 214 engaged with bone anchor 12 provides an electrical pathway to bone anchor 12 are also possible. In addition, while not previously discussed it should be appreciated that one non-limiting example of a neuro-stimulation/monitoring apparatus that can be used in connection with anchor extenders 14, 16, 214 includes the NIMT™-Spine System commercially available from Medtronic Spinal and Biologics, 1800 Pyramid Place, Memphis, Tenn., 38132. Further details regarding another non-limiting example of a neuro-stimulation/monitoring apparatus that can be used in connection with anchor extenders 14, 16, 214 may be found in U.S. Pat. No. 5,474,558, the contents of which are incorporated herein by reference in their entirety.

Referring further to FIGS. 1 and 4-7 collectively, bone anchor 12 includes a proximal receiver 110 and a distal bone engaging member 112. Receiver 110 receives the connecting member 114 from space 40 between anchor extenders 14, 16. In the illustrated embodiment, receiver 110 forms a saddle that houses a portion of bone engaging member 112 and connecting member 114. Receiver 110 receives the connecting member 114 therethrough in an orthogonal or transverse orientation to longitudinal axis 38 and in an orientation that extends generally parallel with the spinal column. In one embodiment, connecting member 114 is an elongated spinal rod, and bone anchor 12 includes a bone screw portion extending from a distally facing end of receiver. The bone screw portion can be a multi-axial type screw pivotally received and carried by receiver 110 so that the receiver and bone screw are pivotal relative to one another. In another embodiment, the bone screw portion is non-pivotal or fixed relative to the receiver. Furthermore, connecting member 114 can be received in, on, or about the receiver 110 for engagement thereto with an engaging member (not shown) such as an externally threaded set screw. However, other embodiments contemplate engaging members that include one or more components in the form of a nut, cap, non-threaded member, friction fit member, twist-lock member, or combinations thereof that engage the receiver. Furthermore, the connecting member 114 can be rigid, semi-rigid, flexible, elastic, non-compression load bearing, or of other suitable form for extending between and stabilizing adjacent portions of the spinal column when secured thereto with one or more bone anchors.

In the illustrated embodiment, receiver 110 includes a pair of opposite side portions 116, 118 sized and spaced to accommodate connecting member 114 and the engaging member. Side portion 116 includes a pair of oppositely positioned detents (not shown) configured to receive elongated tabs 94, 96 of anchor engaging portion 24 of anchor extender 14 and side portion 118 includes a pair of oppositely positioned detents 119 configured to receive elongated tabs (not shown) of anchor engaging portion 32 of anchor extender 16. Side portions 116, 118 each include an internal thread profile 120, 122 to threadingly receive the engaging member. Receiver 110 includes a hole 124 extending on longitudinal axis 38 that opens through a distally facing surface 126 of receiver 110. Hole 124 is sized and shaped to receive bone engaging member 112 therethrough while supporting head 128 of bone engaging member 112 in receiver 110. Near the distally facing surface 126 at the bottom of receiver 110, hole 124 is surrounded by a retaining member 130. Retaining member 130 can be a C-ring, washer, lip, or flange formed separately from or as an integral part of receiver 110 to support head 128 while allowing bone engaging member 112 to be positioned in any one of an infinite number of angular positions relative to receiver 110 and longitudinal axis 38. Other embodiments contemplate other engagement relationships between the bone engaging member 112 and receiver 110. In one embodiment, bone engaging member 112 is formed as a single, integral unit with receiver 110 and extends along longitudinal axis 38 in a co-axial arrangement. In another embodiment, bone engaging member 112 is captured in receiver 110 with a retaining member that allows pivotal movement relative to receiver 110 in a single plane or in a predetermined number of planes or directions relative to longitudinal axis 38.

In the particular illustrated embodiment of bone engaging member 112, it includes an initial configuration that allows pivoting movement in receiver 110 and is thereafter rigidly or semi-rigidly fixed in position when connecting member 114 is seated in receiver 110. Receiver 110 includes a crown 132 positioned on and around the proximal side of head 128. Crown 132 includes a proximal side that projects into a passage 134 defined between side portions 116, 118. When the engaging member is threadingly engaged to receiver 110, it pushes connecting member 114 in passage 134 against the proximal side of crown 132. Crown 132 is in turn pushed against the proximal side of head 128, which seats head 128 firmly against retaining member 130. The proximal side of head 128 may include a plurality of ridges or grooves that bite into a distally facing surface of crown 132 to enhance locking of bone engaging member 112 in position in receiver 110. In another embodiment, at least some motion between the receiver 110 and bone engaging member 112 is maintained by crown 132 when connecting member 114 is secured in receiver 110 with the engaging member. Still other embodiments contemplate that crown 132 can be omitted and that connecting member 114 is seated directly against head 128 of bone engaging member 112 or against a bottom surface 136 of receiver 110 that extends on a distal side of passage 134 between side portions 116, 118.

Bone engaging member 112 is shown as a bone screw with proximal head 128 and an elongated threaded shaft 138 extending distally from head 128 located in receiver 110. Other embodiments contemplate other forms for bone engaging member 112, such as a hook, post, tack, cerclage, staple, anchor, or other suitable bone engaging structure. Bone engaging member 112 can be a separate member that is connected with receiver 110, or formed as an integral, one-piece construct with receiver 110.

Referring now collectively to FIGS. 4-5, further details regarding engagement of anchor extender 14 with receiver 110 of bone anchor 12 will be provided. More particularly, anchor extender 14 may be positioned adjacent to bone anchor 12 with anchor engaging portion 24 in its first configuration such that side portion 116 can be positioned between engaging members 66, 68. Once anchor extender 14 is positioned relative to bone anchor 12 in this manner, elongated pin 34 can be distally displaced relative to elongated body 18 as indicated by directional arrow A in order to move anchor engaging portion 24 to its second position and into engagement with opposite sides of side portion 116 as discussed above. Engagement of anchor extender 14 with bone anchor 12 could occur either before or after bone anchor 12 is engaged with underlying bone or bony tissue. If engagement occurs before engagement of bone anchor 12 with underlying bone or bony tissue, anchor extender 14 can be used for, amongst other things, placing bone anchor 12 and guiding connecting member 114 to bone anchor 12. If engagement occurs after engagement of bone anchor 12 with underlying bone or bony tissue, anchor extender 14 can be used for, amongst other things, guiding connecting member 114 to bone anchor 12. Additionally, in one or more forms, anchor extender 14 can also be used neural monitoring of the placement of bone anchor 12 either during or after its engagement to underlying bone. While FIG. 1 illustrates the use of anchor extender 14 with anchor extender 16, it should be understood that use of anchor extender 14 alone is also possible and contemplated. For example, and without limitation, it should be understood that anchor extender 14 could be individually used with bone anchor 12 for positioning bone anchor 12, guiding connecting member 114 to receiver 110, and/or neural monitoring in connection with the placement of bone anchor 12. While not previously discussed, it should be appreciated that engagement of anchor extenders 16, 214 with bone anchor 212 and their subsequent use could be carried out in manners similar to those described in connection with anchor extender 14.

In the embodiment illustrated in FIG. 1, connecting member 114 may initially be positioned through space 40 between anchor extenders 14, 16 at a location between inner surfaces 44, 46 at or near proximal ends 20, 28 of anchor extenders 14, 16. Since inner surfaces 44, 46 of anchor extenders 14, 16 are spaced farther apart than the alignment surface portions 56, 58, the surgeon has greater latitude in initially positioning connecting member 114 through anchor extenders 14, 16. As connecting member 114 is advanced distally between anchor extenders 14, 16 toward receiver 110, tapered surface portions 52, 54 center connecting member 114 between anchor extenders 14, 16 and align it with passage 134 of receiver 110. Alignment surface portions 52, 54 maintain and guide connecting member 114 into passage 134 as connecting member 114 is seated in receiver 110.

Referring to FIG. 11, there is shown another embodiment spinal surgical system 310 employing multiple bone anchors 12 engaged to respective ones of the vertebrae V1, V2, V3. Although three anchor bone anchors 12 and vertebrae are shown, systems employing one, two, or four or more bone anchors 12 are also contemplated. Anchor extenders 14, 16 extend proximally from respective ones of the bone anchors 12 through the tissue of the patient and skin S to locate the proximal ends of anchor extenders 14, 16 outside the patient. Incisions are made to accommodate insertion of bone anchors 12 and engagement of anchor extenders 14, 16 therewith, and to extend between anchor extenders 14, 16 to receive connecting member 114. Connecting member 114 is placed between anchor extenders 14, 16 outside the patient in a transverse orientation to anchor extenders 14, 16. Connecting member 114 is advanced along anchor extenders 14, 16 and through skin S and the tissue to the implantation location adjacent anchors 12, as indicated by connecting member 114'. Anchor extenders 14, 16 also provide a pathway to allow placement of engaging members therealong to secure connecting member 114' to the respective bone anchor 12.

FIG. 12 shows an example of another embodiment spinal surgical system 410 that employs two bone anchors 12 engaged to respective ones of two vertebrae V1 and V2. Connecting member 114 is placed between anchor extenders 14, 16 engaged to a first one of bone anchors 12 with the connecting member 114 oriented in generally parallel orientation to the longitudinal axis of anchor extenders 14, 16. As connecting member 114 is advanced toward the vertebrae, connecting member 114 is pivoted from its initial orientation below skin S and tissue of the patient so that connecting member 114 extends from one of the bone anchors 12 to the other bone anchor 12, as indicated by connecting member 114'. In this procedure, an incision between anchor extenders 14, 16 engaged to the first one of bone anchors 12 and anchor extenders 14, 16 engaged to the second one of bone anchors 12 can be omitted. Other embodiments also contemplate that this procedure could be employed in procedures using one bone anchor 12 to which anchor extenders 14, 16 are engaged, or more than two bone anchors 12 to which anchor extenders 14, 16 are engaged.

The anchor extenders, instruments, devices, apparatuses, systems and methods described herein also have application with other types of instruments and implants, and may be used in other portions of the body besides the spine. The anchor extenders, instruments, devices, apparatuses, systems and methods described herein may also be used in surgical procedures involving animals, or in demonstrations for training, education, marketing, sales and/or advertising purposes. In addition, the anchor extenders, instruments, devices, apparatuses, systems and methods may also be used on or in connection with a non-living subject such as a cadaver, training aid or model, or in connection with testing of surgical systems, surgical procedures, orthopedic devices and/or apparatus.

In one embodiment, a spinal surgical system includes a connecting member including an elongated body having a length sized to extend between at least two vertebrae. The system also includes a bone anchor including a distal bone engaging portion engageable to bony structure and a receiver extending proximally from the bone engaging portion. The receiver includes a passage between opposite arms of the receiver with the passage opening at opposite sides of the arms of the receiver and with the passage further opening at a proximal end of the receiver. The system further includes a pair of elongated members each extending along a longitudinal axis between a proximal end and an opposite distal end. Each of the elongated members has a locking member and an elongated body, and the elongated body extends between the proximal and distal ends and includes a bifurcated distal end portion extending from a proximal portion. The bifurcated distal end portion includes a pair of engaging members flexibly movable relative to the proximal portion between a first configuration for receiving a respective one of the arms of the receiver and a second configuration for engaging with the respective one of the arms of the receiver. The locking member extends through the proximal portion and is axially displaceable relative to the elongated body between a first position and a second position in engagement with each of the engaging members to retain the engaging members in the second configuration.

In another embodiment, an anchor extender includes an elongated body extending along a longitudinal axis between a proximal end and an opposite distal end. The elongated body includes a proximal portion, a pair of engaging members extending distally from the proximal portion, and an internal passage extending through the proximal portion. In addition, the engaging members are movable relative to one another between a first configuration and a second anchor engaging configuration. The anchor extender further includes an elongated pin axially displaceable relative to the elongated body. The elongated pin extends through the internal passage and along the longitudinal axis between a first end positioned proximal of the proximal end of the elongated body and a second end configured for engagement with the engaging members. The engaging members are moved from the first configuration to the second configuration upon distal displacement of the elongated pin relative to the elongated body.

In still another embodiment, an anchor extender includes an elongated body comprised of an electrically non-conductive material and extending along a longitudinal axis between a proximal end and an opposite distal end. The elongated body includes a proximal portion and a pair of engaging members extending distally from the proximal portion, and the engaging members are movably flexible relative to the proximal portion and cooperate to define an anchor engaging portion. The anchor extender also includes an elongated pin positioned in and axially displaceable relative to the elongated body between a first position and a second position, and the elongated pin is comprised of an electrically conductive material. The elongated pin includes a distal end engageable with the engaging members to retain the anchor engaging portion in an anchor engaging configuration when the elongated pin is in the second position. In addition, the anchor extender includes a contact member comprised of an electrically conductive material and positioned on a first one of the engaging members in the anchor engaging portion. The contact member is engaged by the distal end of the elongated pin when the elongated pin is in the second position to provide an electrically conductive pathway from the proximal end of the elongated body to the anchor engaging portion.

Any theory, mechanism of operation, proof, or finding stated herein is meant to further enhance understanding of the present invention and is not intended to make the present invention in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A spinal surgical system, comprising:
a connecting member including an elongated body having a length sized to extend between at least two vertebrae;
a bone anchor including a distal bone engaging portion engageable to bony structure and a receiver extending proximally from said bone engaging portion, said receiver including a passage between opposite arms of said receiver with said passage opening at opposite sides of said arms of said receiver and with said passage further opening at a proximal end of said receiver;
a pair of elongated members each extending along a longitudinal axis between a proximal end and an opposite distal end, each of said elongated members having a locking member and an elongated body, said elongated body extending between said proximal and distal ends and including a bifurcated distal end portion extending from a proximal portion, said bifurcated distal end portion including a pair of engaging members flexibly movable relative to said proximal portion between a first configuration for receiving a respective one of said arms of said receiver and a second configuration for engaging with said respective one of said arms of said receiver, wherein said locking member extends through said proximal portion and is axially displaceable relative to said elongated body between a first position and a second position in engagement with each of said engaging members to retain said engaging members in said second configuration, wherein each of said engaging members includes a passage for receiving a portion of said locking member.

2. The system of claim 1, wherein said passages of said engaging members are axially aligned when said engaging members are in said second configuration.

3. The system of claim 1, wherein said locking member includes a tapered distal end configured to axially align said passages and move said engaging members to said second configuration upon distal displacement of said locking member from said first position to said second position.

4. The system of claim 1, wherein said passage of a first one of said engaging members is positioned proximally of said passage of a second one of said engaging members.

5. The system of claim 4, wherein said first one of said engaging members includes a second passage positioned distally of said passage of said second one of said engaging members.

6. The system of claim 1, wherein a first one of said engaging members includes a receptacle opening toward a second one of said engaging members, and said second one of said engaging members includes a transverse tab positionable in said receptacle when said engaging members are in said second configuration.

7. The system of claim 1, wherein said locking member includes a tapered distal end configured to move said engaging members from said first configuration to said second configuration upon distal displacement of said locking member from said first position to said second position.

8. The system of claim 7, wherein said locking member includes a wedge member positioned proximally of said tapered distal end.

9. The system of claim 8, wherein a first one of said engaging members includes a first surface extending obliquely to said longitudinal axis, a second one of said engaging members includes a second surface positioned opposite of said first surface and extending obliquely to said longitudinal axis, and said wedge member is configured to engage with said first and second surfaces to move said engaging members from said second configuration to said first configuration upon proximal displacement of said locking member from said second position to said first position.

10. The system of claim 1, wherein said elongated body is comprised of an electrically non-conductive material and said locking member is comprised of an electrically conductive material.

11. The system of claim 10, wherein at least one of said elongated members includes a flexible tab comprised of an electrically conductive material positioned on a first one of said engaging members, and said locking member engages with said flexible tab when said locking member is in said second position to provide an electrically conductive pathway between said proximal end of said elongated member and said bone anchor.

12. The system of claim 1, wherein upon engagement with said receiver of said bone anchor said elongated members define a space therebetween that extends to said passage of said receiver, wherein said space and said passage of said receiver are sized to receive said connecting member therethrough so that said connecting member is movable from said space through said proximal end opening of said passage of said receiver into said receiver.

13. An anchor extender, comprising:
an elongated body extending along a longitudinal axis between a proximal end and an opposite distal end, said elongated body including a proximal portion, a pair of engaging members extending distally from said proximal portion, and an internal passage extending through said proximal portion, said engaging members being movable relative to one another between a first configuration and a second anchor engaging configuration;
an elongated pin axially displaceable relative to said elongated body, said elongated pin extending through said internal passage and along said longitudinal axis between a first end positioned proximal of said proximal end of said elongated body and a second end configured for engagement with said engaging members; and
wherein said engaging members are moved from said first configuration to said second configuration upon distal displacement of said elongated pin relative to said elongated body, wherein a first one of said engaging members includes a first passage, a second passage, and an opening positioned between said first and second passages, a second one of said engaging members includes a projection extending transversely to said longitudinal axis, said projection including a third passage positionable in said opening when said engaging members are in said second configuration, and said elongated pin is positioned in said passages of said engaging members when said engaging members are in said second configuration.

14. The anchor extender of claim 13, wherein said engaging members extend obliquely to said longitudinal axis and one another in said first configuration and substantially parallel to said longitudinal axis and one another in said second configuration.

15. The anchor extender of claim 13, wherein said elongated pin includes an enlarged portion adjacent said second end and each of said engaging members includes a ramp surface extending obliquely to said longitudinal axis, said enlarged portion of said elongated pin engaging with said ramp surfaces to move said engaging members from said second configuration to said first configuration upon proximal displacement of said elongated pin relative to said elongated body.

16. An anchor extender, comprising:
an elongated body extending along a longitudinal axis between a proximal end and an opposite distal end, said elongated body including an electrically non-conductive external surface, a proximal portion and a pair of engaging members extending distally from said proximal portion, said engaging members being movably flexible relative to said proximal portion and cooperating to define an anchor engaging portion;
an elongated pin positioned in and axially displaceable relative to said elongated body between a first position and a second position, said elongated pin comprised of an electrically conductive material and including a distal end engageable with said engaging members to retain said anchor engaging portion in an anchor engaging configuration when said elongated pin is in said second position; and
a contact member comprised of an electrically conductive material and positioned on a first one of said engaging members in said anchor engaging portion;
wherein said contact member is engaged by said distal end of said elongated pin when said elongated pin is in said second position to provide an electrically conductive pathway from said proximal end of said elongated body to said anchor engaging portion.

17. The anchor extender of claim 16, wherein said contact member includes a first portion positioned in a passage of said first one of said engaging members and a second portion extending obliquely to said first portion and from said passage through a sidewall surrounding said passage.

18. The anchor extender of claim 16, wherein said elongated pin is structured to move said engaging members toward one another upon distal movement of said elongated pin from said first position to said second position and away from one another upon proximal movement of said elongated pin from said second position to said first position.

19. The anchor extender of claim 16, wherein said elongated body is comprised of an electrically non-conductive material.

20. The anchor extender of claim 16, wherein said elongated body is comprised of an electrically conductive material and includes an electrically insulative material covering said electrically conductive material.

\* \* \* \* \*